United States Patent [19]

Hamper et al.

[11] Patent Number: 5,600,008
[45] Date of Patent: Feb. 4, 1997

[54] BENZOYL DERIVATIVES AND SYNTHESIS THEREOF

[75] Inventors: Bruce C. Hamper, Kirkwood; Kindrick L. Leschinsky, Ellisville, both of Mo.

[73] Assignee: Monsanto Company, St. Louis, Mo.

[21] Appl. No.: 403,037

[22] Filed: Mar. 13, 1995

Related U.S. Application Data

[63] Continuation of Ser. No. 277,724, Jul. 20, 1994, abandoned, which is a continuation-in-part of Ser. No. 169,285, Dec. 20, 1993, abandoned, which is a continuation of Ser. No. 763,762, Sep. 25, 1991, Pat. No. 5,281,571, which is a continuation-in-part of Ser. No. 600,031, Oct. 18, 1990, abandoned.

[51] Int. Cl.$^6$ ..................................................... C07C 45/45
[52] U.S. Cl. ............................................ 568/314; 568/315
[58] Field of Search .................................... 568/314, 315

[56] References Cited

U.S. PATENT DOCUMENTS 5,146,002  9/1992  Yamada .

FOREIGN PATENT DOCUMENTS

WO92/06962  4/1992  WIPO ........................ C07D 231/16

OTHER PUBLICATIONS

Joshi et al., *Indian J. Chem.* (1976) 14B:1004–1006 "Studies in Fluorinated β–Diketones & Related Compounds: Part V– Synthesis & Special Studies of Fluorine Containing 1,4-Diazepines/Diazepinium Perchlorates & Their 6–Halogeno Derivatives".

Joshi et al. *J. Inorg. Nucl. Chem.* (1977) 39:803–810 "Studies in Fluorinated β–Diketones and Related Compounds–IV".

European Search Report for PCT/US95/08839 (1995).

Chemical Abstracts, vol. 122, No. 21, 22 May 1995, Columbus, Ohio, US, abstract no. 265364.

Chemical Abstracts, vol. 119, No. 3, 19 Jul. 1995, Columbus, Ohio, US, abstract no. 027827.

J. Chem. Soc. Perkin Trans. 1, (JCPRB4); 74; (15); pp. 1769–1771, La Trobe Univ. (1974).

Heterocycles (HTCYAM, 03855414); 85; vol. 23 (11); pp. 2828–2833, Univ. Tasmania (1985).

Chemische Berichte, vol. 47, (1914) Weinheim De, pp. 3040–3052.

*Primary Examiner*—James H. Reamer
*Attorney, Agent, or Firm*—Grace L. Bonner; Monsanto Company

[57] ABSTRACT

The present invention relates to novel 4-halo-2-fluoro-5-alkoxybenzoyl compounds and their methods of manufacture. These compounds are useful for the preparation of agricultural chemicals and medicines, particularly as intermediates for an active class of arylhaloalkylpyrazole and aryl alkylsulfonylpyrazole herbicides.

5 Claims, No Drawings

BENZOYL DERIVATIVES AND SYNTHESIS THEREOF

This application is a divisional of application Ser. No. 08/277,724, filed Jul. 20, 1994, now abandoned, which is a continuation-in-part of Ser. No. 08/169,285, filed Dec. 20, 1993, now abandoned, which is a continuation of application Ser. No. 07/763,762, filed Sep. 25, 1991, now Pat. No. 5,281,571, which is a continuation-in-part of application Ser. No. 07/600,031, filed Oct. 18, 1990, now abandoned.

FIELD OF THE INVENTION

The present invention relates to novel benzoyl derivatives and their methods of manufacture. These compounds are useful for the preparation of agricultural chemicals and medicines and particularly, as intermediates for an active class of arylhaloalkylpyrazole and aryl alkylsulfonylpyrazole herbicides.

BACKGROUND OF THE INVENTION

In recent years it has been found that one class of active herbicides are the substituted phenylpyrazoles, the phenyl and pyrazole moieties of which contain a variety of substituents.

Methods of manufacturing these phenylpyrazoles commonly involve chemical conversions of one or more radicals substituted on the phenyl and/or pyrazole moieties, e.g., by halogenation, esterification, etc. It is also known to prepare these compounds from substituted acetophenones by interaction with various compounds, including various esters which contribute the desired substituent radical to the 5-position of the pyrazole radical via cyclization of an intermediate phenyl diketone. For example, various halo- and/or alkyl-substituted acetophenones have been reacted with (halo) acetic acid esters to produce the corresponding phenyl diketone which is cyclized with hydrazine to yield phenylpyrazoles substituted in the 5-position of the pyrazole radical with (halo) alkyl groups.

It has recently been disclosed that certain 3-substituted aryl-5-substituted pyrazoles are particularly useful for broadspectrum control of a variety of weeds at very low application rates in a number of agronomically important crops. The aryl group is typically the phenyl radical substituted with halogen, alkyl, alkoxy and ester groups, substituents which are also commonly found on the pyrazole moiety. Particularly effective within this class of compounds are esters of 2-chloro-5-(4-halo-1-methyl-5-(trifluoromethyl)-1H-pyrazol-3-yl)-4-fluorobenzoic acid. These particular compounds are most readily available from 2-fluoro-5-alkylacetophenones and their derivatives. The literature, however, does not provide methods of preparation of these intermediates or related compounds that could provide the desired pyrazolylbenzoic acid esters. Thus, there is a need in the art for the discovery of novel intermediates and for efficient methods for the preparation of these substituted arylpyrazole compounds.

The present invention describes intermediates useful for production of compounds within this new class of herbicides.

SUMMARY OF THE INVENTION

The present invention relates to a class of benzoyl derivatives of Formula I and synthesis methods therefor:

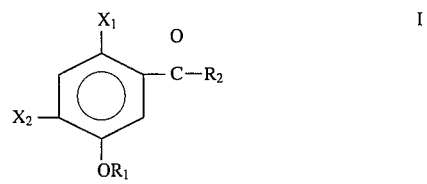

wherein $X_1$ and $X_2$ are H or a halogen atom, $R_1$ is a $C_{1-6}$alkyl group optionally substituted with halogen or alkoxy or alkoxyalkyl having up to 6 carbon atoms; and $R_2$ is $C_{1-6}$ alkyl or $C_{1-6}$ haloalkyl, H or —$CH_2COR_3$; wherein $R_3$ is a $C_{1-6}$ haloalkyl group.

A preferred subgenus of the benzoyl compounds in this invention are those according to Formula I wherein:

$X_1$ is fluorine;

$X_2$ is Cl or Br;

$R_1$ is methyl;

$R_2$ is H, halogen, methyl or —$CH_2COR_3$ and $R_3$ is $CF_3$, $CF_2Cl$, $CF_2H$ or $C_2F_5$.

The most preferred species herein are those according to Formula I wherein $X_1$ is fluoro, $X_2$ is chloro, $R_1$ is $CH_3$ and $R_2$ is —$CH_2COCF_3$.

As readily apparent to those skilled in the art, when $R_2$ in Formula I is hydrogen, the resulting compound (Formula IA below) is a substituted benzaldehyde; when $R_2$ is methyl (Formula IB below), the compound is a substituted acetophenone and when $R_2$ is the —$CH_2COR_3$ radical, the resulting compound is a substituted phenyldiketone (Formula IC below). All of these compounds have the substituted benzoyl radical as a common structural feature, hence, for simplicity and convenience herein all of these compounds will be referred to collectively as benzoyl derivatives.

To applicants' knowledge all of the substituted benzoyl derivatives herein are novel compounds.

DETAILED DESCRIPTION OF THE INVENTION

Compounds of Formula I wherein $R_1$ is a methyl group, $X_1$ is fluoro, $X_2$ is H or a halogen and $R_2$ is H (Formula IA) or methyl (Formula IB) are prepared from 2-substituted-4-fluoroanisoles of Formula II, which are known in the art, according to the following equation

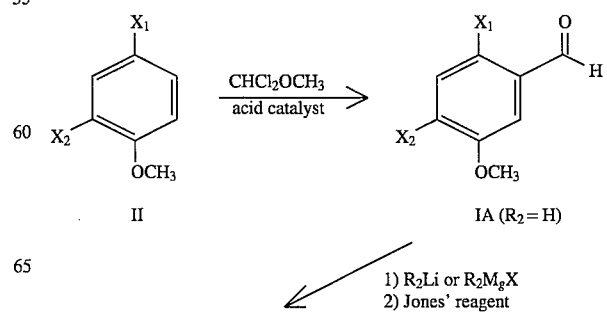

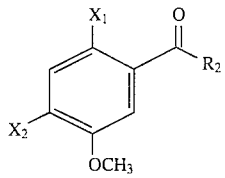

IB

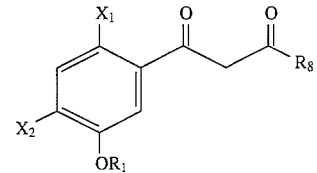

IC

Typically, 2,4-dihalo-5-alkoxybenzaldehydes of Formula IA are prepared by alkylation of 2,4-dihaloanisoles of Formula II with a 1,1-dihaloalkylalkylether in the presence of an acid catalyst at a temperature in the range of −100° C. to 100° C., preferably −78°C. to 50°C. An alkylating agent such as 1,1-dichloromethyl methyl ether is preferred and can be employed in a range of one molar equivalent to an excess. The acid catalyst may be a Lewis acid such as $TiCl_4$, $SnCl_4$, $FeCl_3$ or a Bronstead acid such as $H_2SO_4$. The amount of catalyst can be from less than 0.1 mole % to excesses greater than 100 mole % relative to the 2,4-dihaloanisole. Any inert solvent may be used in this reaction that does not markedly hinder the reaction from proceeding or the reaction can be carried out neat. Preferred solvents include, but are not limited to, dichloromethane, dichloroethanes, nitrobenzene or hydrocarbons. Products are isolated by treatment of the reaction mixture with water and isolation of the product by standard methods. Yields of the desired materials can be favorably improved by treatment of the crude product with mineral acid, such as conc. H2SO4 or HCl to convert any geminal dichlorides to aldehydes. Isolation can then be caried out in the usual manner.

Acetophenones and alkyl aryl ketones of Formula I wherein $R_2$ is a lower alkyl group can be prepared from the above obtained benzaldehydes by a sequence of known reaction types. The benzaldehyde is treated with an organometallic reagent such as an alkyl lithium or alkyl Grignard reagent to give an intermediate benzyl alcohol. Methyl lithium and methyl Grignard are preferred for preparation of the acetophenones. The reactions can be carried out in any suitable anhydrous solvent such as THF, diethyl ether, toluene. Oxidation of the benzyl alcohol with any suitable oxidizing agent gives the desired aryl alkyl ketone of Formula I. Preferred oxidants include, but are not limited to, chromium oxide, chromium oxide in sulfuric acid, potassium permanganate, potassium dichromate, etc. Reaction temperature is in the range of −78° C. to the boiling point of the inert solvent, preferably 0° C. to 100° C. The reaction period may be chosen from the range of a few minutes to several weeks depending on the amounts of reagents, reaction temperature, etc.

Compounds of Formula IC are prepared from compounds of Formula IB by reaction with $R_3COZ$ wherein Z is a $C_{1-6}$ alkoxy or $C_{6-8}$ aryloxy group or a halogen atom or by reaction with anhydride $(R_3CO)_2O$, where in both formulae $R_3$ is $C_{1-6}$ haloalkyl.

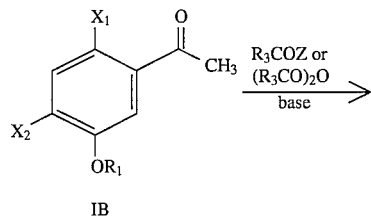

IB

Thus, diketones of Formula IC can be prepared by treatment of 2-fluoro-4-(H or halogen)-5-alkylacetophenones with an ester, an anhydride or an acid halide in the presence of a base. Any suitable solvent or mixture of solvents can be employed; the preferred solvents are anhydrous ether, alcohols, dimethylsulfoxide, toluene, benzene, etc. The reaction is carried out in the presence of a base such as an alkali alkoxide, alkali amide or alkali hydride with the alkali alkoxides such as sodium methoxide being preferred. Reaction temperature is in the range of −100° C. to 200° C., preferably −78° C. to the reflux temperature of the solvent. The reaction period may be chosen from the range of a few minutes to several weeks depending on the amounts of reagents, reaction temperature, etc.

Compounds of Formula IC are meant to include all possible tautomers, such as enols and all possible salts wherein the cation is an alkali metal or other suitable organic or inorganic cationic species.

The compounds of Formula IC can be converted to pyrazolylbenzoyl esters useful as synthetic herbicides by the following reactions.

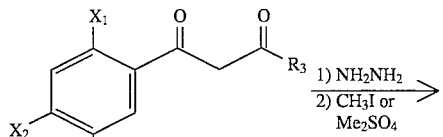

IC

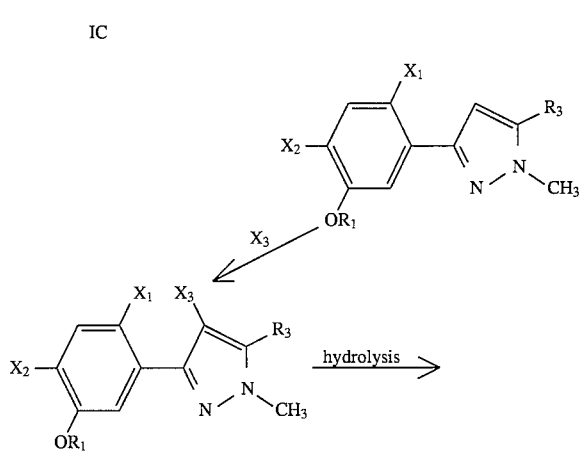

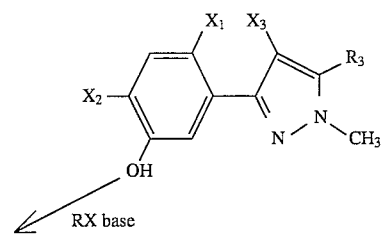

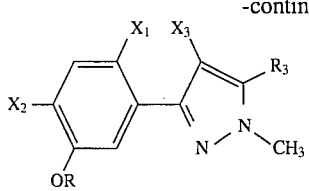

In the above formulae, $R_1$, $R_3$, $X_1$ and $X_2$ are as previously defined for Formula I, $X_3$ is halogen and R is an alkyl or substituted alkyl group.

The following Examples 1–9 describe specific working embodiments for the preparation of representative compounds according to this invention.

EXAMPLE 1

Preparation of 4-Chloro-2-fluoro-5-methoxy-benzaldehyde

To a nitrogen purged 3 L round bottom flask equipped with a mechanical stirrer and a gas scrubber was added 114 g of titanium(IV) chloride followed by 48 g of 2-chloro-4-fluoroanisole. The stirred mixture was cooled in an ice water bath and treated dropwise with of 68.4 g of α, α-dichloromethyl methyl ether. After stirring for 90 minutes, the resultant slurry was treated with 200 mL of methylene chloride and the reaction allowed to reach room temperature. The mixture was treated with an additional 500 mL of methylene chloride, added dropwise to ice water in a 4 L beaker and the resultant mixture extracted three times with methylene chloride. The combined organic extracts were washed with water, 10% $Na_2CO_3$, dried and concd to give a crude oily solid. Trituration with hexanes yielded 42 g (74%) of 4-chloro-2-fluoro-5-methoxybenzaldehyde as a white solid. An analytical sample was obtained by bulb-to-bulb distillation to give a white, crystalline solid: mp 120.0–122.0° C.; $^1$H NMR ($CDCl_3$) δ 3.93 (s,3H), 7.25 (d, 1H, J=9.4 Hz), 7.34 (d, 1H, 5.9 Hz), 10.28 (s, 1H).

Anal. Calcd for C $C_8H_6O_2Cl_1F_1$:
C, 50.95; H, 3.21; Cl, 18.80.
Found: C, 50.83; H, 3.24; Cl, 18.90.

EXAMPLE 2

Preparation of 1-(4-Chloro-2-fluoro-5methoxyphenyl) ethanone

A stirred solution of 10.4 g of 4-chloro-2-fluoro-5-methoxybenzaldehyde in 150 mL of anhydrous THF was cooled in a dry ice-acetone bath and treated with 35 mL of a 3M solution of methyl magnesium chloride in THF over a period of one minute. The ice bath was removed and the mixture allowed to warm to room temperature. After warming, the solution was slowly poured into ice water. The water slurry was extracted three times with diethyl ether, the ether extracts dried and concd to afford a crude oil. Crystallization from hexanes yielded 10.8 g (95.6%) of 4-chloro-2-fluoro-5-methoxy-α-methyl-benzenemethanol: mp 68.5°–69.5° C. This benzenemethanol intermediate was dissolved in 100 mL of acetone, cooled in an ice water bath and treated dropwise with 50 mL of freshly prepared Jones'reagent (prepared from 6.7 g of $CrO_3$, 6 mL of $H_2SO_4$ and 50 mL of water), keeping the temperature below 10° C. After stirring for 2 hrs., the solution was diluted with water and extracted three times with methylene chloride. The organic extracts were dried and concd to give a crude product. Recrystallization from methanol yielded 9.66 g (90.3%) of 1-(4-chloro-2-fluoro-5-methoxyphenyl) ethanone as a white solid: mp 96.5–98.5 ° C.; $^1$HNMR ($CDCl_3$) δ 2.50 (d, 3H, 5.4 Hz), 3.80 (s, 3H), 7.10 (d, 1H, 10.1 Hz), 7.30 (d, 1H, 6.3 Hz).

Anal. calcd for C $C_9H_8O_2Cl_1F_1$: C
C, 53.55; H, 3.98.
Found: C, 53.45; H, 3.96.

EXAMPLE 3

Preparation of 1-(4-Chloro-2-fluoro-5-methoxyphenyl)-4,4,4-trifluoro-1,4-butanedione A solution of 21.8 g of 1-(4-chloro-2-fluoro-5-methoxyphenyl) ethanone in 100 ml of anhydrous diethyl ether was cooled in an ice bath. The stirred mixture was treated all at once with 28.1 g of ethyl trifluoroacetate. After stirring for a few minutes, 50 mL of 25% sodium methoxide in methanol (0.20 mol) was added and the solution was allowed to stir overnight. The mixture was quenched with 150 ml of water and 100 ml conc. HCL. The reaction mixture was extracted three times with diethyl ether and the combined organic layers separated, dried, and concd to afford a tan solid. The crude solid was recrystalized from methanol to give 23.5 g (73.2%) of 1- (4-chloro-2-fluoro-5-methoxyphenyl)-4,4,4-trifluoro-1,4-butanedione as a yellow solid: mp 122–123° C.; $^1$HNMR ($CDCl_3$) δ3.80 (d, 3H, 2 Hz), 6.60 (d, 1H, 2 Hz), 7.10 (dd, 1H, 11 Hz, 2 Hz), 7.40 (dd, 1H, 4 Hz, 2 Hz).

Anal. Calcd for C $C_{11}H_6O_3Cl_1F_4$: C, 44.39; H, 2.03.
Found: C, 44.23; H, 2.36.

Examples 4–6 were prepared by alkylation of the corresponding anisole in a manner analogous to the process of Example 1.

Example 7 was prepared according to the two-step addition-oxidation sequence in a manner analogous to the process of Example 2.

Examples 8 and 9 were prepared according to the process analogous to that in Example 3.

Physical properties for the compounds of Examples 4–9 are shown in the table below.

TABLE

PHYSICAL DATA FOR 2,4-DIHALO-5-METHOXY-BENZALDEHYDES AND THEIR DERIVATIVES

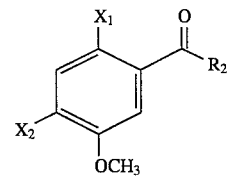

| EXAMPLE | $X_1$ | $X_2$ | $R_2$ | mp/refractive index |
| --- | --- | --- | --- | --- |
| 4 | Cl | F | H | 102.0° C.–104.0° C. |
| 5 | F | F | H | 85° C.–86° C. |
| 6 | Cl | Cl | H | 113° C.–115° C. |
| 7 | F | Cl | Et | 82° C. |
| 8 | F | Cl | $CH_2COCF_2CF_3$ | 114.0° C. |
| 9 | F | Cl | $CH_2COCF_2Cl$ | 112.0° C. |

The novel 2,4-dihalo-5-alkoxybenzaldehydes, 2,4-dihalo-5-alkoxyacetophenones and benzoyl derivatives of the present invention are useful as intermediates for the preparation or manufacture of agricultural chemicals and medicines, particularly the substituted phenylpyrazole type herbicides. These intermediates allow direct introduction of a 5'-alkoxy substituent on the phenyl ring of the phenylpyrazole which can be converted to 5'-substituted oxyphenyl pyrazoles such as 5'-propargyloxyphenylpyrazoles or pyrazolylphenoxyacetic acids or esters.

As will be appreciated by those skilled in the art, various modifications of the invention described herein may be made without departing from the spirit and scope thereof.

We claim:

1. Process for preparing compounds according to Formula IC

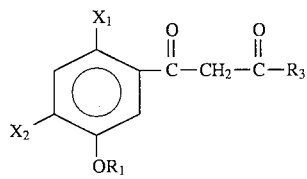

comprising acylating a compound according to Formula IB

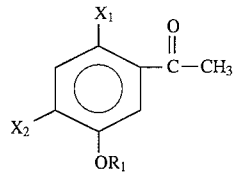

by reaction with $(R_3CO)_2O$ or $R_3COZ$ wherein $X_1$ and $X_2$ are H or halogen;

$R_1$ is $C_{1-6}$ alkyl and $R_3$ is $C_{1-6}$ haloalkyl, and

Z is halogen, $C_{1-6}$ alkoxy or $C_{6-8}$ aryloxy in an inert solvent in the presence of a strong base at a temperature between $-78°$ C. and $200°$ C. and after workup recovering said compound according to Formula IC.

2. Process according to claim 1 wherein $X_1$ is fluoro, $X_2$ is chloro, $R_1$ is methyl and $R_3$ is $-CF_3$.

3. Process according to claim 1 wherein said compounds according to Formula IB are prepared by reacting a compound according to Formula II

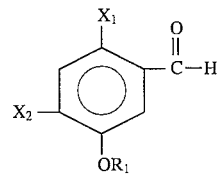

wherein $X_1$, $X_2$ and $R_1$ are as previously defined, with an organometallic reagent, followed by reaction with an oxidation agent in an inert solvent.

4. Process according to claim 3 wherein said organometallic reagent is an alkyl lithium or alkyl Grignard reagent and said oxidation agent is Jones' reagent.

5. Process according to claim 4 wherein said organic metallic reagent is methyl lithium or methyl Grignard.

* * * * *